United States Patent [19]

Brown

[11] Patent Number: 4,978,794
[45] Date of Patent: Dec. 18, 1990

[54] NOVEL β-(2-ALKENYL)BIS(2-ISOCARANYL)BORANES

[75] Inventor: Herbert C. Brown, West Lafayette, Ind.

[73] Assignee: Aldrich Chemical Company, Inc., Milwaukee, Wis.

[21] Appl. No.: 498,966

[22] Filed: Mar. 26, 1990

[51] Int. Cl.⁵ ................................................. C07F 5/02
[52] U.S. Cl. ........................................ 568/1; 568/813; 568/878
[58] Field of Search ............................. 568/1, 813, 878

[56] References Cited

U.S. PATENT DOCUMENTS 4,713,380 12/1987 Brown ........................................ 568/1
4,772,752 9/1988 Brown ................................. 568/1 X Primary Examiner—Paul F. Shaver
Attorney, Agent, or Firm—Niblack & Niblack

[57] ABSTRACT

2-Alkenylbis(2-isocaranyl)boranes represented by the formula:

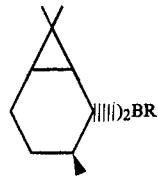

wherein R is 2-alkenyl. The compounds undergo asymmetric 2-alkenylboration with a variety of aldehydes and afford the corresponding alcohols in 94–99% ee.

12 Claims, No Drawings

NOVEL β-(2-ALKENYL)BIS(2-ISOCARANYL)BORANES

BACKGROUND OF THE INVENTION

Over the past few years, asymmetric allyl-, crotyl-, and higher allyl boron reagents have proven to be exceptionally valuable in the context of acyclic stereoselection. Driven by the rapidly growing demand for highly enantiomerically pure substances in multi-step natural product syntheses, the development of superior allylborane reagents, which can achieve enantio- and diasterioselectivities approaching 100% has become both desirable and challenging.

A number of asymmetric allylboron reagents have been reported by various investigators. See Hoffmann, R. W. et al., *Chem. Ber.* 1981, 114, 375; Brown, H. C. et al., *Am. Chem. Soc.*, 1983, 105, 2092; *Idem. J. Org. Chem.* 1984, 49, 4089; Roush, W. R. et al., *Am. Chem. Soc.* 1985, 107, 8786; Brown, H. C. et al., *Ibid.* 1986, 108, 293; Rousch, W. R. et al., *Ibid.* 294; Brown, H. C. et al., *J. Org. Chem.* 1987, 52. 319; *Idem. Ibid.* 3701; Garcia, J. et al., *Ibid.* 4831; Brown, H. C. et al., *S. J. Am. Chem. Soc.* 1988, 110, 1535; Roush, W. R. et al., *Ibid.* 3979; Short, R. P. et al, *J. Am. Chem. Soc.* 1989 111, 1982; and Corey, E. J. et al., *J. Am. Chem. Soc.* 1989, 5495. While asymmetric allylborations of aldehydes with comparatively high enantioselectivities has been achieved with prior art reagents, each of these reagents require the preparation of the chiral auxiliaries in several steps and some even require resolution.

The present invention provides a new class of reagents, B-(2-alkenyl)bis(2-isocaranyl)borane, which undergoes reaction with a variety of aldehydes to furnish the corresponding homoalkenylic alcohols in 94–99% ee. The enantioselectivities realized with this reagent are significantly higher than those realized previously with B-allyldiisopinocampheylborane and B-allylbis(4-ioscaranyl)borane (reported by Brown, H. C. et al, *J. Org. Chem* 1986 51, 432).

SUMMARY OF THE INVENTION

The present invention provides novel B-(2-alkenyl) bis(2-isocaranylboranes represented by the formula:

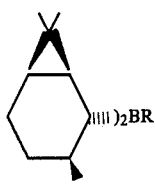

wherein R is 2-alkenyl. The novel compounds are useful as reagents for the asymmetric 2-alkenylboration of aldehydes to the corresponding optically active alcohols of high optical purity ($\geq 96\%$).

The term "2-alkenyl", as used herein refers to allyl, crotyl, higher crotyl and γ,γ-disubstituted allyl represented by the formulae: (shown with a boron substituent for clarity.

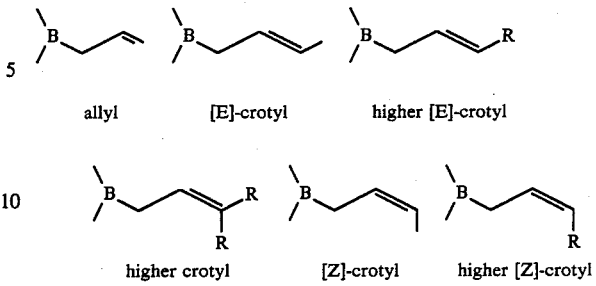

The 2-alkenyl groups can be substituted with $C_1$ to $C_{18}$ straight or branched chain alkyl or cycloalkyl.

The term " γ,γ-disubstituted allyl refers to allyl groups represented by the formula

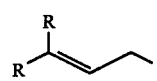

wherein R is $C_1$ to $C_{18}$ straight or branched chain alkyl or cycloalkyl.

The designation "Icr" refers to isocaranyl.

The starting material for bis(2-isocaranyl)borane, (+)-2-carene is prepared via the base-induced isomerization of (+)-3-carene, a naturally occurring material. (+)-2-Carene can be purchased from Aldrich Chemical Company, Milwaukee, Wis.

Generally speaking, the compounds of this invention are prepared by conversion of bis-(2-isocaranylborane) (2-$^d$Icr$_2$BH) into the desired B-(2-alkenyl)bis(2-isocaranyl)boranes. The reaction can be conveniently run at temperatures of from −100° C. to 25° C. Lower temperatures are preferred, and most preferably, reactions are run at −100° C. which surprisingly provides consistent optical purity of $\geq 99\%$ ee for all aldehydes investigated to date.

The new reagents of the present invention possess a relatively hindered boron atom that is flanked on both sides by substituents, in contrast to the prior art reagents B-allyldiisopinocampheylborane and B-allylbis(4-isocaranyl)borane, and achieve greater enantioselectivities on allylboration.

They are useful as intermediates in the preparation of optically active homoallylic alcohols of high optical purity, generally $\geq 96\%$ ee.

DETAILED DESCRIPTION OF PREFERRED EMBODIMENTS

Unless otherwise specified, the reaction flasks and other equipment were stored in an oven at 150° C. overnight and assembled in a stream of dry nitrogen gas. Special techniques used in handling air-sensitive materials are described in Brown, H. C. et al., "*Organic Synthesis via Boranes*"; Wiley-Interscience: New York, 1975 and were generally followed. All solvents were distilled and stored under nitrogen. The capillary GC analyses for the determination of optical purities of the derivatized product homoallylic alcohols were performed on a Hewlett-Packard 5890 gas chromatograph.

EXAMPLE 1

Preparation of B-Allylbis(2-isocaranyl)borane

To borane-methyl sulfide (10.3) mL, 9.8 M, 100 mmol) in tetrahydrofuran (200 mL), cooled to $-10°$ C., was added (+)-2-carene (30 g, 220 mmol), $\alpha_D^{23}+92°$ (neat), over a period of 10 minutes while stirring the reaction mixture. Following completion of the addition, stirring was discontinued and the flask containing the reaction mixture was stored at 0° C. for 24 h. White needles of 2-$^d$Icr$_2$BH separated out. The supernatant liquid was then decanted by a double-ended needle and the crystals were washed with anhydrous ether (3×50 mL) chilled to 0° C. The solid was dried under vacuum at room temperature to obtain 2-$^d$Icr$_2$BH (24.3 g, 85%) of essentially 100% optical purity (ee). Next, 2-$^d$Icr$_2$BH ester (Dale, J. A. et al., *J. Org. Chem.* 1969, 34, 2543) on a capillary methyl silicone column (50 M × 0.25 cm)established the compound to be 98% ee.

EXAMPLES 3-9

Following the method of Example 2, the compound of Example 1 was reacted with other representative aldehydes. All of the products are known and the individual isolation techniques have been fully described in Jadhav., P. K. et al., *J. Org. Chem.* 1986, 51, 432, which is incorporated by reference herein. Table I sets forth a comparison of the asymmetric allylborations of representative aldehydes with B-allylbis(2-isocaranyl)borane (Example 1), and the prior art reagents, B-allyldiisopinocampheyl borane and B-allylbis(4-isocaranyl)borane.

TABLE I

A Comparison of the Asymmetric Allylborations of Representative Aldehydes with Chiral B-Allyldialkylboranes 1-3 at −78° C.

| | | reagent, % ee | | |
|---|---|---|---|---|
| aldehyde | alcohol | $^d$Ipc$_2$BAll$^a$ (2) | 4-$^d$Icr$_2$BAll (3) | 2-$^d$Icr$_2$BAll (1) |
| acetaldehyde | 4-penten-2-ol | [R], 92$^b$ (93) | [R], 94$^b$ (99) | [S], 98$^b$ |
| propionaldehyde | 5-hexen-3-ol | [R], (86) | [R], (91) | [S], 94$^d$ |
| n-butyraldehyde | 1-hepten-4-ol | [R], 86$^c$ (87) | [R], 88$^c$ (89) | [S], 94$^c$ |
| 2-methylpropionaldehyde | 2-methyl-5-hexen-3-ol | [S], 88$^b$ (90) | [S], 95$^b$ (97) | [R], 94$^b$ |
| 2,2-dimethylpropionaldehyde | 2,2-dimethyl-5-hexen-3-ol | [S], (83) | [S], (88) | [R], 99$^b$ |
| acrolein | 1,5-hexadien-3-ol | [S], 92$^b$ | [S], 93$^b$ (86) | [R], 95$^b$ |
| benzaldehyde | 1-phenyl-3-buten-1-ol | [S], 94$^b$ (96) | [S], 87 | [R], 95$^b$ |

$^a$Use of $^l$Ipc$_2$BAll [derived from (−)-α-pinene] provides the opposite enantiomer.
$^b$Determined by capillary GC analysis of the corresponding (+)-Mosher ester.
$^c$Determined by capillary GC analysis of the corresponding menthylcarbonates. See ref 10b.
$^d$Determined by capillary GC analysis of the corresponding TPC ester. See ref 10c.
Values in parentheses are % ee of the corresponding alcohols based on comparison of optical rotations.

(14.3 g, 50 mmol) was suspended in tetrahydrofuran (20 mL) and treated with methanol (4 mL) at 0° C. in a dropwise fashion over a period of 20 minutes while vigorously stirring the reaction mixture. After the evolution of hydrogen had ceased (0° C., 6 h), a clear solution formed, indicating completion of the methanolysis. The solvent was stripped off under vacuum (14 mm, 1h; 1 mm, 2h) to obtain B-methoxybis(2-isocaranyl)borane (15.8g, 100%). The methoxy derivative was dissolved in anhydrous ether (50 mL) and cooled to −78° C. To this solution was added allylmagnesium bromide in ether (48 mL, 1.0 M, 48 mmol) in a dropwise manner. The reaction mixture was stirred for 15 min at −78° C. and then warmed to room temperature (1 h) to obtain an essentially quantitative yield of β-allylbis(2-isocarnyl)borane. The identity was confirmed by $^{11}$B NMR (δ+80 ppm).

EXAMPLE 2

The reaction mixture containing the compound of Example 1 (without removing the precipitated magnesium salts) was cooled to −78° C. and acetaldehyde in slight excess (2.8 mL, 50 mmol) was added dropwise with stirring. The stirring was continued for 3 h at −78° C. and the reaction mixture was treated with 3 N NaOH (20 mL) and 30% H$_2$O$_2$ (40 mL). The reaction mixture was next refluxed for 3 h to ensure the completion of oxidation. The organic layer was separated, washed with brine, dried over anhydrous magnesium sulfate and concentrated. The residue was finally fractionally distilled (bp 94° C. at 90 mm) to obtain [S]-(+)-4-penten-2-ol. Yield: 3.2 g (74%). GC analysis of its Mosher

EXAMPLE 10

Preparation of B-methoxybis(-2-isooaranyl)borane

A 250 mL flask equipped with a side arm and magnetic bar was charged with BMS (10 mL, 100 mmol) and 90 mL THF and cooled to 0° C. (+)-2-Carene (30g, 220 mmol, $\alpha_D^{23}+92°$ (neat)] was added with stirring over a period of 5 min. Following the completion of the addition, the reaction flask was stored at 0° C. for 24 h without stirring. A white crystalline solid of 2-$^d$Icr$_2$BH of essentially 100% ee separated out. The supernatants were decanted, the solid washed with anhydrous ether (3×30 mL). The solid 2-Icr$_2$BH was suspended in THF (50 mL) and methanol (8 mL, 200 mmol) was added dropwise with stirring at 0° C. After complete evolution of H$_2$ had ceased (0° C., 6 h), a clear solution formed indicating completion of methanolysis. The solvents were removed under vacuum (14 mm Hg, 1 h); 1 mm Hg, 2 h). The residue (quantitative yield) was dissolved in sufficient anhydrous ethyl ether to make a 1M standard solution.

EXAMPLE 11

Preparation of (E)-Crotylbis(2-isocaranyl)borane

To a stirred solution of potassium tert-butoxide (2.8 g, 25 mmol), THF ( 7 mL) and trans-2-butene (6.5 mL, 50 mmol) was added n-butyllithium (25 mmol in THF at −78° C. After complete addition of the n-BuLi, the reaction was warmed to −45° for 5 min. to insure complete metallation. The resulting solution was recooled to −78° C. and to it was added dropwise B-methoxybis(2isocaranyl)borane (Example 10, 1 M, 27 mmol) in ether. To the resulting "ate" complex, the boron trifluoride etherate (40 mL, 3.5 mmol) was added dropwise to provide the title trialkylborane. The trialkylborane was immediately utilized for condensation with the aldehyde.

EXAMPLE 12

Preparation of [2S,3R]-(+)-3-Methyl-4-penten-2-ol

Acetaldehyde (2 mL, 35 mmol) was added dropwise at −78° C. to the compound of Example 11. The reaction mixture was stirred at −78° C. for 3 h and then treated with methanol (4 mL) and allowed to warm to room temperature. The resulting mixture was oxidized by alkaline hydrogen peroxide. The organic layer was separated, washed with water ( 10 mL), brine (10 mL), and dried over anhydrous magnesium sulfate. After evaporation of solvent, the residue was carefully distilled to obtain the [2S,3R]-(+)-2-methyl-4-penten-2-ol: yield 75%; bp 78° C./85 mm, disasterioselectivity ≧99%; 96% ee (determined by capillary GC analysis of the corresponding Mosher ester).

EXAMPLE 13

Preparation of [3S,4R]-4-Methyl-5-hexen-3-ol

To (E)-Crotylbis(2-isocaranyl)borane (Example 11, 25 mmol) was slowly added propionaldehyde (1.8 mL, 25 mmol) at 78° C. The stirring continued for 2 h. at −78° C. The resulting borinate was oxidized with alkaline hydrogen peroxide to provide the title compound: bp 105° C. (bath, 80 mm Hg); yield, 75%, 98% ee (determined by capillary GC analysis).

EXAMPLES 14 AND 15

Preparation of (Z)-Orotylbis(2-isocaranyl)borane and [2S,3S]-3-Methyl-4-penten-2-ol To a stirred mixture of potassium tert-butoxide (2.8 g, 25 mmol), THF (7 mL) and cis-2-butene (6.5 mL, 50 mmol), n-butyllithium in THF (2.3 M, 25 mmol) was added slowly at −78° C. After complete addition, the reaction mixture was warmed to −45° C. for 5 min, recooled to −78° C. and methoxybis(2-isocarany)-borane (1 M in ether, 27 mmol) was added slowly with stirring. 25 After the reaction mixture was stirred at −78° C. for 30 min, BF₃.OEt₂ (6 mL, 33 mmol) was added dropwise, then acetaldehyde (35 mmol) was added dropwise at −78° C. and stirring continued for 2 h at −78° C. The reaction mixture was quenched with methanol (6 mL), reaction mixtures was allowed to warm to room temperature and oxidized by successive addition of hydrogen peroxide (8 mL) and NaOH (16 mL, 3N). The workup described in Example 12 furnished [2S,3S]-3-methyl-6-penten-2-ol: yield, 75%; bp. 78./85 mm, 94% ee.

EXAMPLE 16

Preparation of [3S,4S]-4-methyl-5-hexen-3-ol

The title compound was prepared following the method of Examples 14 and 15, substituting proprionaldehyde (1.8 mL, 25 mmol) for acetaldehyde: yield, 78%; bp 105° C. (bath, 80 mm Hg); diasteroselectivity ≧99%; 96% ee (determined by capillary GC analysis).

EXAMPLES 17–22

The following representative enantiomerically pure compounds are prepared following the method of Example 1:
B-(3,3-Dimethylallyl)bis(2-isocaranyl)borane; B-(3,3-Diethylallyl)bis(2-isocaranyl)borane; B-(3-Cyclohexyl-[Z]-crotyl)bis(2-isocaranyl)borane; B-(3-Phenyl-[E]-crotyl)bis(2-isocaranyl)borane; B-(3-Iso-amyl-[E]-crotyl)bis(2-isocaranyl)borane; B-(3-iso-propyl-[Z]-crotyl)bis(2-isocaranyl)borane.

EXAMPLES 23–28

While the above reactions can be run at temperatures ranging from −100° C. to 25° C., homoallylic alcohols with optical purities approaching 100% ee (≧99%) are achieved practically instantaneously at −100° C. The enantioselectivies achieved by the process of this invention with representative aldehydes at −78° C. and −100° C. are summarized in Table II.

TABLE II

A Comparison of the Enantioselectivities Achieved in the Allylborations of Representative Aldehydes with ᵈIpc₂BAll (ᵈ1), 4-ᵈIcr₂BAll (2) and 2-ᵈIcr₂BAll (3) at −78° C. (Procedure A) and −100° C. in Et₂O Under Salt-Free Conditions

| | | reagents, % ee of products | | | | | | | |
|---|---|---|---|---|---|---|---|---|---|
| | | ᵈIpc₂BAll (ᵈ1) | | | 4-ᵈIcr₂BAll (2) | | | 2-ᵈIcr₂BAll (3) | |
| aldehyde | product | −78° C.ᶜ | −100° C. | abs. conf. | −78° C. | −100° C. | abs. conf. | −78° C. | −100° C. | abs. conf. |
| acetaldehyde | 4-penten-2-ol | 92 | ≧99ᵉ | R | 94 | ≧99 | R | 98 | ≧99 | S |
| n-butyraldehyde | 1-hepten-4-ol | 86 | 96ᶠ | R | 88 | 98 | R | 94 | ≧99 | S |
| isobutyraldehyde | 2-methyl-5-hexen-3-ol | 88 | 96ᵉ | S | 95 | 98 | S | 94 | ≧99 | R |
| pivalaldehyde | 2,2-dimethyl-5-hexen-3-ol | 83 | ≧99ᵉ | S | 88 | ≧99 | S | 99 | ≧99 | R |
| acrolein | 1,5-hexadien-3-ol | 92 | 96ᵉ | S | 93 | 98 | S | 95 | ≧99 | R |
| benzaldehyde | 1-phenyl-3-buten-1-ol | 94 | 96ᵉ | S | 87 | 98 | S | 95 | ≧99 | R |

The invention claimed is:

1. B-(2-Alkenyl)bis(2-isocaranyl)boranes represented by the formula

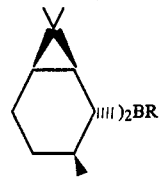

wherein R is 2-alkenyl.

2. A compound of claim 1, B-allylbis(2-isocaranyl)borane.

3. A compound of claim 1, B-[Z]-crotylbis(2-isocaranyl)borane.

4. A compound of claim 1, B-[E]-crotylbis(2-isocaranyl)borane.

5. A compound of claim 1, B-[Z]-higher crotylbis(2-isocaranyl)borane.

6. A compound of claim 1, B-[E]-higher crotylbis(2-isocaranyl)borane.

7. A compound of claim 1, B-($\gamma,\gamma$-disubstituted allyl)bis(2-isocaranyl)borane.

8. A compound of claim 7, B-($\gamma,\gamma$-dimethylallyl)bis(2-isocaranyl)borane.

9. A process of converting aldehydes to optically active alcohols of essentially 100% ee comprising reacting an aldehyde with a B-(2-alkenyl)bis(2-isocaranyl)borane.

10. The process of claim 9, wherein said reaction is carried out at a temperature of from $-100°$ C. to $25°$ C.

11. The process of claim 9 wherein said reaction is carried out at a temperature of from $-78°$ C. to $-100°$ C.

12. The process of claim 9 wherein said reaction is carried out at $-100°$ C.

* * * * *